United States Patent
Garaj et al.

(10) Patent No.: US 9,797,863 B2
(45) Date of Patent: *Oct. 24, 2017

(54) GRAPHENE SUPPORTED ARTIFICIAL MEMBRANES AND USES THEREOF

(71) Applicant: President and Fellows of Harvard College, Cambridge, MA (US)

(72) Inventors: Slaven Garaj, Cambridge, MA (US); Daniel Branton, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,820

(22) Filed: Sep. 5, 2014

(65) Prior Publication Data
US 2015/0101931 A1 Apr. 16, 2015

Related U.S. Application Data

(63) Continuation of application No. 13/702,928, filed as application No. PCT/US2011/039621 on Jun. 8, 2011, now Pat. No. 8,828,211.

(60) Provisional application No. 61/352,636, filed on Jun. 8, 2010, provisional application No. 61/352,791, filed on Jun. 8, 2010.

(51) Int. Cl.
| | | |
|---|---|---|
| *G01N 27/447* | (2006.01) | |
| *G01N 33/487* | (2006.01) | |
| *G01N 27/453* | (2006.01) | |

(52) U.S. Cl.
CPC ..... *G01N 27/44791* (2013.01); *G01N 27/447* (2013.01); *G01N 27/453* (2013.01); *G01N 33/48721* (2013.01); *Y10S 977/734* (2013.01)

(58) Field of Classification Search
CPC ............... G01N 27/453; G01N 27/447; G01N 27/44791; G01N 33/48721; C01B 31/0438–31/0492; H01L 29/1606
See application file for complete search history.

(56) References Cited

U.S. PATENT DOCUMENTS

| | | | |
|---|---|---|---|
| 3,815,024 | A | 6/1974 | Bean et al. |
| 3,856,633 | A | 12/1974 | Fletcher, III |
| 4,456,522 | A | 6/1984 | Blackburn |
| 4,521,729 | A | 6/1985 | Kiesewetter et al. |
| H201 | H | 1/1987 | Yager |
| 4,661,235 | A | 4/1987 | Krull et al. |

(Continued)

FOREIGN PATENT DOCUMENTS

| | | |
|---|---|---|
| CN | 101474898 A | 7/2009 |
| DE | 30 28 569 A1 | 2/1982 |

(Continued)

OTHER PUBLICATIONS

U.S. Appl. No. 14/151,259, Akeson et al.
(Continued)

*Primary Examiner* — J. Christopher Ball
(74) *Attorney, Agent, or Firm* — Clark & Elbing LLP (57) ABSTRACT

The invention features the use of graphene, a one atom thick planar sheet of bonded carbon atoms, in the formation of artificial lipid membranes. The invention also features the use of these membranes to detect the properties of polymers (e.g., the sequence of a nucleic acid) and identify transmembrane protein-interacting compounds.

24 Claims, 5 Drawing Sheets

(56) References Cited

U.S. PATENT DOCUMENTS

| | | | |
|---|---|---|---|
| 4,874,499 A | 10/1989 | Smith et al. | |
| 4,926,114 A | 5/1990 | Doutre | |
| 5,001,048 A | 3/1991 | Taylor et al. | |
| 5,111,221 A | 5/1992 | Fare et al. | |
| 5,221,447 A | 6/1993 | Hjerten | |
| 5,234,566 A | 8/1993 | Osman et al. | |
| 5,356,776 A | 10/1994 | Kambara et al. | |
| 5,376,878 A | 12/1994 | Fisher | |
| 5,378,342 A | 1/1995 | Ikematsu et al. | |
| 5,503,744 A | 4/1996 | Ikematsu et al. | |
| 5,612,179 A | 3/1997 | Simons | |
| 5,795,782 A | 8/1998 | Church et al. | |
| 5,833,826 A | 11/1998 | Nordman | |
| 5,911,871 A | 6/1999 | Preiss et al. | |
| 6,015,714 A | 1/2000 | Baldarelli et al. | |
| 6,054,035 A | 4/2000 | Kambara | |
| 6,156,502 A | 12/2000 | Beattie | |
| 6,190,865 B1 | 2/2001 | Jendrisak et al. | |
| 6,203,993 B1 | 3/2001 | Shuber et al. | |
| 6,210,896 B1 | 4/2001 | Chan | |
| 6,214,545 B1 | 4/2001 | Dong et al. | |
| 6,221,603 B1 | 4/2001 | Mahtani | |
| 6,221,635 B1 | 4/2001 | Rovera et al. | |
| 6,238,866 B1 | 5/2001 | Yeh et al. | |
| 6,263,286 B1 | 7/2001 | Gilmanshin et al. | |
| 6,267,872 B1 | 7/2001 | Akeson et al. | |
| 6,355,420 B1 | 3/2002 | Chan | |
| 6,362,002 B1 | 3/2002 | Denison et al. | |
| 6,403,311 B1 | 6/2002 | Chan | |
| 6,428,959 B1 | 8/2002 | Deamer | |
| 6,464,842 B1 | 10/2002 | Golovchenko et al. | |
| 6,503,409 B1 | 1/2003 | Fleming | |
| 6,528,258 B1 | 3/2003 | Russell | |
| 6,617,113 B2 | 9/2003 | Deamer | |
| 6,627,067 B1 | 9/2003 | Branton et al. | |
| 6,673,615 B2 | 1/2004 | Denison et al. | |
| 6,746,594 B2 | 6/2004 | Akeson et al. | |
| 6,783,643 B2 | 8/2004 | Golovchenko et al. | |
| 6,863,833 B1* | 3/2005 | Bloom | B81B 1/004 204/403.08 |
| 7,189,503 B2 | 3/2007 | Akeson et al. | |
| 7,238,485 B2* | 7/2007 | Akeson | B01L 3/502707 435/283.1 |
| 7,468,271 B2 | 12/2008 | Golovchenko et al. | |
| 7,625,706 B2 | 12/2009 | Akeson et al. | |
| 7,846,738 B2 | 12/2010 | Golovchenko et al. | |
| 7,947,454 B2 | 5/2011 | Akeson et al. | |
| 8,394,640 B2 | 3/2013 | Golovchenko et al. | |
| 8,673,556 B2 | 3/2014 | Akeson et al. | |
| 8,828,211 B2 | 9/2014 | Garaj et al. | |
| 8,969,091 B2 | 3/2015 | Golovchenko et al. | |
| 8,986,528 B2 | 3/2015 | Denison et al. | |
| 9,046,483 B2 | 6/2015 | Denison et al. | |
| 2002/0039737 A1 | 4/2002 | Chan et al. | |
| 2002/0081744 A1 | 6/2002 | Chan et al. | |
| 2002/0119455 A1 | 8/2002 | Chan | |
| 2003/0044816 A1 | 3/2003 | Denison et al. | |
| 2003/0059822 A1 | 3/2003 | Chan et al. | |
| 2003/0066749 A1 | 4/2003 | Golovchenko et al. | |
| 2003/0104428 A1 | 6/2003 | Branton et al. | |
| 2004/0033492 A1 | 2/2004 | Chen | |
| 2004/0110205 A1 | 6/2004 | Wang | |
| 2005/0053961 A1 | 3/2005 | Akeson et al. | |
| 2005/0241933 A1 | 11/2005 | Branton et al. | |
| 2006/0003458 A1 | 1/2006 | Golovchenko et al. | |
| 2006/0057585 A1 | 3/2006 | McAllister | |
| 2006/0063171 A1 | 3/2006 | Akeson et al. | |
| 2007/0054276 A1 | 3/2007 | Sampson | |
| 2007/0190542 A1 | 8/2007 | Ling et al. | |
| 2007/0194225 A1 | 8/2007 | Zorn | |
| 2009/0142504 A1* | 6/2009 | Ervin | H01B 1/122 427/430.1 |
| 2010/0028681 A1 | 2/2010 | Dai et al. | |
| 2012/0234679 A1 | 9/2012 | Garaj et al. | |
| 2015/0307931 A1 | 10/2015 | Akeson et al. | |

FOREIGN PATENT DOCUMENTS

| | | |
|---|---|---|
| GB | 2 232 769 A | 12/1990 |
| WO | WO-94/25862 A1 | 11/1994 |
| WO | WO-98/35012 A2 | 8/1998 |
| WO | WO-99/24823 A1 | 5/1999 |
| WO | WO-00/09757 A1 | 2/2000 |
| WO | WO-00/56937 A2 | 9/2000 |
| WO | WO-00/78668 A1 | 12/2000 |
| WO | WO-00/79257 A1 | 12/2000 |
| WO | WO-01/18251 A1 | 3/2001 |
| WO | WO-01/42782 A1 | 6/2001 |
| WO | WO-01/59684 A2 | 8/2001 |
| WO | WO-02/42496 A2 | 5/2002 |
| WO | WO-03/000920 A2 | 1/2003 |
| WO | WO-03/003446 A2 | 1/2003 |
| WO | WO-2004/077503 A2 | 9/2004 |
| WO | WO-2009/035647 A1 | 3/2009 |
| WO | WO-2009/045472 A1 | 4/2009 |
| WO | WO-2009/046094 A1 | 4/2009 |
| WO | WO-2009/138760 A1 | 11/2009 |
| WO | WO-2010/138136 A1 | 12/2010 |
| WO | WO-2011/046706 A1 | 4/2011 |

OTHER PUBLICATIONS

Akeson et al., "Microsecond time-scale discrimination among polycytidylic acid, polyadenylic acid, and polyuridylic acid as homopolymers or as segments within single RNA molecules," Biophys J. 77(6):3227-33 (1999).

Andersen, "Sequencing and the single channel," Biophys J. 77(6):2899-901 (1999).

Auld et al., "A neutral amino acid change in segment IIS4 dramatically alters the gating properties of the voltage-dependent sodium channel," Proc Natl Acad Sci USA. 87(1):323-7 (1990).

Bayley et al., "Stochastic sensors inspired by biology," Nature. 413(6852):226-30 (2001).

Beckmann et al., "Alignment of conduits for the nascent polypeptide chain in the ribosome-Sec61 complex," Science. 278(5346):2123-6 (1997).

Bensimon et al., "Alignment and sensitive detection of DNA by a moving interface," Science. 265(5181):2096-8 (1994).

Benz et al., "Mechanism of sugar transport through the sugar-specific LamB channel of *Escherichia coli* outer membrane," J Membr Biol. 100(1):21-9 (1987).

Benz et al., "Pore formation by LamB of *Escherichia coli* in lipid bilayer membranes," J Bacteriol. 165(3):978-86 (1986).

Bezrukov et al., "Counting polymers moving through a single ion channel," Nature. 370(6487):279-81 (1994).

Boulain et al., "Mutagenesis by random linker insertion into the lamB gene of *Escherichia coli* K12," Mol Gen Genet. 205(2):339-48 (1986).

Boulanger et al., "Characterization of ion channels involved in the penetration of phage T4 DNA into *Escherichia coli* cells," J Biol Chem. 263(20):9767-75 (1988).

Boulanger et al., "Ion channels are likely to be involved in the two steps of phage T5 DNA penetration into *Escherichia coli* cells," J Biol Chem. 267(5):3168-72 (1992).

Boyd et al., "Determinants of membrane protein topology," Proc Natl Acad Sci USA. 84(23):8525-9 (1987).

Branton et al., "Biochemical sensors. Adapting to nanoscale events," Nature. 398(6729):660-1 (1999).

Branton et al., "The potential and challenges of nanopore sequencing," Nat Biotechnol. 26(10):1146-53 (2008).

Braun et al., "A common receptor protein for phage T5 and colicin M in the outer membrane of *Escherichia coli* B," Biochim Biophys Acta. 323(1):87-97 (1973).

Charbit et al., "Permissive sites and topology of an outer membrane protein with a reporter epitope," J Bacteriol. 173(1):262-75 (1991).

Charbit et al., "Probing the topology of a bacterial membrane protein by genetic insertion of a foreign epitope; expression at the cell surface," EMBO J. 5(11):3029-37 (1986).

(56) References Cited

OTHER PUBLICATIONS

Dargent et al., "Effect of point mutations on the in-vitro pore properties of maltoporin, a protein of *Escherichia coli* outer membrane," J Mol Biol. 201(3):497-506 (1988).
Dargent et al., "Selectivity for maltose and maltodextrins of maltoporin, a pore-forming protein of *E. coli* outer membrane," FEBS Lett. 220(1):136-42 (1987).
Deamer et al., "Characterization of nucleic acids by nanopore analysis," Acc Chem Res. 35(10):817-25 (2002).
Deamer et al., "Nanopores and nucleic acids: prospects for ultrarapid sequencing," Trends Biotechnol. 18(4):147-51 (2000).
DeBlois et al., "Electrokinetic measurements with submicron particles and pores by the resistive pulse technique," J Colloid Interface Sci. 61(2):323-35 (1977).
DeBlois et al., "Sizes and concentrations of several type C oncornaviruses and bacteriophage T2 by the resistive-pulse technique," J Virol. 23(2):227-33 (1977).
Ehrmann et al., "Genetic analysis of membrane protein topology by a sandwich gene fusion approach," Proc Natl Acad Sci USA. 87(19):7574-8 (1990).
Ferenci et al., "Channel architecture in maltoporin: dominance studies with lamB mutations influencing maltodextrin binding provide evidence for independent selectivity filters in each subunit," J Bacteriol. 171(2):855-61 (1989).
Feucht et al., "Pore formation associated with the tail-tip protein pb2 of bacteriophage T5," J Biol Chem. 265(30):18561-7 (1990).
Fischbein et al., "Electron beam nanosculpting of suspended graphene sheets," Appl Phys Lett. 93:113107 (2008) (3 pages).
Fologea et al., "DNA conformation and base number simultaneously determined in a nanopore," Electrophoresis. 28(18):3186-92 (2007).
Geim et al., "The rise of graphene," Nat Mater. 6(3):183-91 (2007).
Ghadiri et al., "Artificial transmembrane ion channels from self-assembling peptide nanotubes," Nature. 369(6478):301-4 (1994).
Guihard et al., "Involvement of phage T5 tail proteins and contact sites between the outer and inner membrane of *Escherichia coli* in phage T5 DNA injection," J Biol Chem. 267(5):3173-8 (1992).
Hall et al., "Alamethicin. A rich model for channel behavior," Biophys J. 45(1):233-47 (1984).
Hamill et al., "Improved patch-clamp techniques for high-resolution current recording from cells and cell-free membrane patches," Pflugers Arch. 391(2):85-100 (1981).
Harrington et al., "The F pilus of *Escherichia coli* appears to support stable DNA transfer in the absence of wall-to-wall contact between cells," J Bacteriol. 172(12):7263-4 (1990).
Healy et al., "Solid-state nanopore technologies for nanopore-based DNA analysis," Nanomedicine (Lond). 2(6):875-97 (2007).
Heinemann et al., "Open channel noise. IV. Estimation of rapid kinetics of formamide block in gramicidin A channels," Biophys J. 54(4):757-64 (1988).
Heinemann et al., "Open channel noise. V. Fluctuating barriers to ion entry in gramicidin A channels," Biophys J. 57(3):499-514 (1990).
Henry et al., "Blockade of a mitochondrial cationic channel by an addressing peptide: an electrophysiological study," J Membr Biol. 112(2):139-47 (1989).
Hornblower et al., "Single-molecule analysis of DNA-protein complexes using nanopores," Nat Methods. 4(4):315-17 (2007) (including Supplementary Materials, 6 pages).
Hoshi et al., "Biophysical and molecular mechanisms of Shaker potassium channel inactivation," Science. 250(4980):533-8 (1990).
Hoshi et al., "Two types of inactivation in Shaker K+ channels: effects of alterations in the carboxy-terminal region," Neuron. 7(4):547-56 (1991).
Howorka et al., "Sequence-specific detection of individual DNA strands using engineered nanopores," Nat Biotechnol. 19(7):636-9 (2001).
International Preliminary Report on Patentability for International Application No. PCT/US2011/039621, dated Dec. 10, 2012 (4 pages).
International Search Report for International Application No. PCT/US2011/039621, dated Nov. 2, 2011 (4 pages).
Kasianowicz et al., "Characterization of individual polynucleotide molecules using a membrane channel," Proc Natl Acad Sci USA. 93(24):13770-3 (1996).
Killmann et al., "Conversion of the FhuA transport protein into a diffusion channel through the outer membrane of *Escherichia coli*," EMBO J. 12(8):3007-16 (1993).
Kubitschek, "Electronic counting and sizing of bacteria," Nature. 182(4630):234-5 (1958).
Lakey et al., "The voltage-dependent activity of *Escherichia coli* porins in different planar bilayer reconstitutions," Eur J Biochem. 186(1-2):303-8 (1989).
Letellier et al., "Channeling phage DNA through membranes: from in vivo to in vitro," Res Microbiol. 154(4):283-7 (2003).
Letellier et al., "Release of respiratory control in *Escherichia coli* after bacteriophage adsorption: process independent of DNA injection," J Bacteriol. 161(1):179-82 (1985).
Li et al., "DNA molecules and configurations in a solid-state nanopore microscope," Nat Mater. 2(9):611-5 (2003).
Li et al., "Ion-beam sculpting at nanometre length scales," Nature. 412(6843):166-9 (2001).
Lopez et al., "Hydrophobic substitution mutations in the S4 sequence alter voltage-dependent gating in Shaker K+ channels," Neuron. 7(2):327-36 (1991).
Marquis et al., "SpoIIIE strips proteins off the DNA during chromosome translocation," Genes Dev. 22(13):1786-95 (2008).
Meller et al., "Rapid nanopore discrimination between single polynucleotide molecules," Proc Natl Acad Sci USA. 97(3):1079-84 (2000).
Meller et al., "Single molecule measurements of DNA transport through a nanopore," Electrophoresis. 23(16):2583-91 (2002).
Meller et al., "Voltage-driven DNA translocations through a nanopore," Phys Rev Lett. 86(15):3435-8 (2001).
Moellerfeld et al., "Improved stability of black lipid membranes by coating with polysaccharide derivatives bearing hydrophobic anchor groups," Biochem Biophys Acta. 857:265-70 (1986).
Movileanu et al., "Detecting protein analytes that modulate transmembrane movement of a polymer chain within a single protein pore," Nat Biotechnol. 18(10):1091-5 (2000).
Nath et al., "Transcription by T7 RNA polymerase using benzo[a]pyrene-modified templates," Carcinogenesis. 12(6):973-6 (1991).
Nauck et al., "Detection of mutations in the apolipoprotein CII gene by denaturing gradient gel electrophoresis. Identification of the splice site variant apolipoprotein CII-Hamburg in a patient with severe hypertriglyceridemia," Clin Chem. 44(7):1388-96 (1998).
Neher et al., "Single-channel currents recorded from membrane of denervated frog muscle fibres," Nature. 260(5554):799-802 (1976).
Novick et al., "Fluorescence measurement of the kinetics of DNA injection by bacteriophage lambda into liposomes," Biochemistry. 27(20):7919-24 (1988).
Ohba et al., "Induction of DNA replication by transcription in the region upstream of the human c-myc gene in a model replication system," Mol Cell Biol. 16(10):5754-63 (1996).
Ollis et al., "Domain of *E. coli* DNA polymerase I showing sequence homology to T7 DNA polymerase," Nature. 313(6005):818-9 (1985).
Ollis et al., "Structure of large fragment of *Escherichia coli* DNA polymerase I complexed with dTMP," Nature. 313:762-6 (1985).
Ovchinnikov et al., The Cyclic Peptides: Structure, Conformation, and Function: P. Gramicidin S (851), Its Analogues, and Tyrocidines A-C (904-906), *The Proteins (Third Edition)* vol. 5, Academic Press, Inc., 547-555 (1982).
Ovchinnikov et al., The Cyclic Peptides: Structure, Conformation, and Function: T. Valinomycin, *The Proteins (Third Edition)* vol. 5, Academic Press, Inc., 563-573 (1982).
Patil et al., "Aqueous stabilization and self-assembly of graphene sheets into layered bio-nanocomposites using DNA," Adv Mater. 21:3159-64 (2009).
Patton et al., "Amino acid residues required for fast Na(+)-channel inactivation: charge neutralizations and deletions in the III-IV linker," Proc Natl Acad Sci USA. 89(22):10905-9 (1992).

(56) References Cited

OTHER PUBLICATIONS

Product Description of Nytran Nylon membranes, <http://www.whatman.com/NytranNylonMembranes.aspx>, accessed Jan. 29, 2009.

Reina et al., "Large area, few-layer graphene films on arbitrary substrates by chemical vapor deposition," Nano Lett. 9(1):30-5 (2009).

Sauer-Budge et al., "Unzipping kinetics of double-stranded DNA in a nanopore," Phys Rev Lett. 90(23):238101-1 (2003) (4 pages).

Shiver et al., "On the explanation of the acidic pH requirement for in vitro activity of colicin E1. Site-directed mutagenesis at Glu-468," J Biol Chem. 262(29):14273-81 (1987).

Sigworth et al., "Open channel noise. III. High-resolution recordings show rapid current fluctuations in gramicidin A and four chemical analogues," Biophys J. 52(6):1055-64 (1987).

Simon et al., "A protein-conducting channel in the endoplasmic reticulum," Cell. 65(3):371-80 (1991).

Sint et al., "Selective ion passage through functionalized graphene nanopores," J Am Chem Soc. 130(49):16448-9 (2008).

Smith et al., "Images of a lipid bilayer at molecular resolution by scanning tunneling microscopy," Proc Natl Acad Sci USA. 84(4):969-72 (1987).

Sukharev et al., "Electroporation and electrophoretic DNA transfer into cells. The effect of DNA interaction with electropores," Biophys J. 63(5):1320-7 (1992).

Tabib-Azar et al., "Synthetic Nanopores for Molecular Spectroscopy," IEEE Sensors Conference, 566-568 (2008).

Taylor et al., "'Reversed' alamethicin conductance in lipid bilayers," Biophys J. 59(4):873-9 (1991).

The Royal Swedish Academy of Sciences, "Scientific Background on the Nobel Prize in Physics 2010: Graphene," Oct. 5, 2010 (11 pages).

Titov et al., "Sandwiched graphene—membrane superstructures," ACS Nano. 4(1):229-34 (2010).

Vercoutere et al., "Rapid discrimination among individual DNA hairpin molecules at single-nucleotide resolution using an ion channel," Nat Biotechnol. 19(3):248-52 (2001).

Wang et al., "Nanopores with a spark for single-molecule detection," Nat Biotechnol. 19(7):622-3 (2001).

Weiss et al., "Molecular architecture and electrostatic properties of a bacterial porin," Science. 254(5038):1627-30 (1991).

West et al., "A cluster of hydrophobic amino acid residues required for fast Na(+)-channel inactivation," Proc Natl Acad Sci USA. 89(22):10910-4 (1992).

White et al., "Single ion-channel recordings using glass nanopore membranes," J Am Chem Soc. 129(38):11766-75 (2007).

Wonderlin et al., "Optimizing planar lipid bilayer single-channel recordings for high resolution with rapid voltage steps," Biophys J. 58(2):289-97 (1990).

Wu et al., "Bacillus subtilis SpoIIIE protein required for DNA segregation during asymmetric cell division," Science. 264(5158):572-5 (1994).

Zavriev et al., "RNA polymerase-dependent mechanism for the stepwise T7 phage DNA transport from the virion into *E. coli*," Nucleic Acids Res. 10(5):1635-52 (1982).

Zwolak et al., "Colloquium: physical approaches to DNA sequencing and detection," available on DOI:10.1103/RevModPhys.80.141 Sep. 2007, published in final edited form as: Rev Mod Phys. 80(1):141-165 (2008) (26 pages).

Lee et al., "Measurement of the elastic properties and intrinsic strength of monolayer graphene," Science. 321(5887):385-8 (2008).

Meyer et al., "The structure of suspended graphene sheets," Nature. 446(7131):60-3 (2007).

\* cited by examiner

GRAPHENE SUPPORTED ARTIFICIAL MEMBRANES AND USES THEREOF

STATEMENT AS TO FEDERALLY FUNDED RESEARCH

This invention was made with government support under HG003703 awarded by National Institutes of Health. The government has certain rights in the invention.

BACKGROUND OF THE INVENTION

The invention relates to the field of artificial lipid bilayer membranes.

Artificial monolayers and bilayers of lipids are frequently used in the discovery of the physiological and pharmacological properties of cell surface and intracellular membrane proteins. Artificial monolayers and bilayers are also key components of many commercial devices including sensitive biosensors that are being used or developed to detect biological warfare agents, to discover membrane receptors that regulate human disease or pathogen function, and to screen pharmaceutical agents to reveal their function, identity, and concentration. During the past forty years, electrophysiological studies of proteins reconstituted into unsupported lipid bilayers have generated detailed information on membrane protein function, ligand-binding, and kinetics. Because the function of membrane proteins plays a critical role in all aspects of development, organ function, and health, studies of proteins reconstituted into lipid bilayers are extensively used to screen for potentially useful drugs as well as to identify targets for drug therapies.

Electrophysiological studies have been used to characterize the properties of single molecules, such as DNA molecules, that can be translocated through transmembrane proteins such as α-hemolysin.

While monolayers are often formed and supported on hydrophobic surfaces, bilayers are more frequently assembled as free-standing membranes. Lipid monolayers and bilayers are labile, delicate structures that are easily damaged. Free-standing bilayer membranes, which are particularly well suited for acquisition of electrophysiological data from membrane proteins and sensitive nanopore detection methods, are especially susceptible to rupture. Therefore, there exists a need in the art for resilient artificial lipid membranes.

SUMMARY OF THE INVENTION

In general, the invention features a device including an artificial membrane on graphene with one or more apertures, e.g., having a dimension of less than 10 µm (e.g., a plurality of apertures arranged in an array). The artificial membrane includes two lipid monolayers, each contacting one face of the graphene, and the two lipid monolayers form a lipid bilayer within an aperture in the graphene. The lipid bilayer can further include a protein (e.g., a transmembrane protein). The transmembrane protein can be an ion channel, a multidrug resistance pump, a cytokine receptor, a receptor from the immunoglobin superfamily, a receptor from the tumor necrosis factor receptor family, a chemokine receptor, a receptor tyrosine kinases, or a TGF beta receptor.

The device can also include at least one pore (e.g., α-haemolysin) disposed in at least one aperture, with, e.g., at most one pore disposed in each of the apertures. A molecule motor can be adjacent to at least one of the pores and can be capable of moving a polymer with respect to the pore. In embodiments where the polymer is a nucleic acid, examples of molecular motors are a DNA polymerase (e.g., E. coli DNA polymerase I, E. coli DNA polymerase I Large Fragment (Klenow fragment), phage T7 DNA polymerase, Phi-29 DNA polymerase, Thermus aquaticus (Taq) DNA polymerase, Thermus flavus (Tfl) DNA polymerase, Thermus Thermophilus (Tth) DNA polymerase, Thermococcus litoralis (Tli) DNA polymerase, Pyrococcus furiosus (Pfu) DNA polymerase, Vent™ DNA polymerase, Bacillus stearothermophilus (Bst) DNA polymerase, AMV reverse transcriptase, MMLV reverse transcriptase, and HIV-1 reverse transcriptase), an RNA polymerase (e.g., T7 RNA polymerase, T3 RNA polymerase, SP6 RNA polymerase, and E. coli RNA polymerase), a ribosome, an exonuclease (e.g., exonuclease Lambda, T7 Exonuclease, Exo III, RecJ$_1$ Exonuclease, Exo I, and Exo T), or a helicase (e.g., E-coli bacteriophage T7 gp4 and T4 gp41 gene proteins, E. coli protein DnaB, E. coli protein RuvB, and E. coli protein rho).

In any of the foregoing, the device can further including a frame (e.g., a non-conductive frame including a ceramic or silicon nitride) supporting the graphene and/or first and second electrodes disposed on opposite sides of the graphene. The frame can be positioned on one face of the graphene forming a compartment for housing liquid for each of the apertures. Multiple compartments can each include an electrode (or other sensor) and are typically fluidically isolated.

In another aspect, the invention features a method of analyzing a target polymer including introducing the target polymer to a pore-containing device of the invention, allowing the target polymer to move with respect to the pore to produce a signal, and monitoring the signal corresponding to the movement of the target polymer. Exemplary devices used in these methods include a molecular motor, e.g., an exonuclease, to control movement of the polymer, e.g., a nucleic acid. The signal monitoring can include measuring a monomer-dependent characteristic (e.g., identity of a monomer or the number of monomers in the polymer) of the target polymer. In one embodiment, the rate of movement of the polymer can be altered before, during, or after the signal monitoring. The method may alternatively be used to study the effect of the polymer on the pore or molecular motor.

In another aspect, the invention features a method of identifying a transmembrane protein-interacting compound by contacting a transmembrane protein positioned in any of the foregoing devices with a compound and measuring at least one activity of the protein (directly or indirectly by its effect on the compound) in the presence of the compound, whereby a change in activity in the presence of the compound indicates that the compound interacts with the protein. Compounds may bind to, inhibit, agonize, react with, or be altered during an interaction with the protein. Alternatively, the compound may affect the integrity or rigidity of the bilayer, thereby indirectly interacting with the protein. In one embodiment, an electric field is applied and the measuring at least one activity of the transmembrane protein includes measuring the electrical resistance of the transmembrane protein.

Similarly, the methods can be used to measure the interaction of compounds with other membrane molecules, e.g., a lipid in the bilayer or a compound conjugated to a lipid. In such methods, the lipid layer may or may not include a pore.

By "across" is meant a measurement or movement not from one face to the other, e.g., in substantially the same plane as a face of graphene.

By "through" is meant a measurement or movement from one face to the opposing face of graphene.

By a "change in activity" is meant a measured difference in a property of an aperture in the presence of a candidate compound when compared to that same property of the aperture in the absence of the candidate compound. A change in activity can be, e.g., an increase or decrease of 1%, 5%, 10%, 25%, 50%, 75%, 100%, or more.

By "cis" is meant the side of an aperture through which a polymer enters the aperture or across the face of which the polymer moves.

By "trans" is meant the side of an aperture through which a polymer (or fragments thereof) exits the aperture or across the face of which the polymer does not move.

By "molecular motor" is meant a molecule (e.g., an enzyme) that physically interacts with a polymer, e.g., a polynucleotide, and is capable of physically moving the polymer with respect to a fixed location. Although not intending to be bound by theory, molecular motors utilize chemical energy to generate mechanical force. The molecular motor may interact with each monomer of a polymer in a sequential manner.

Other features and advantages of the invention will be apparent from the following drawings, detailed description, and the claims.

DETAILED DESCRIPTION OF THE INVENTION

Graphene is a one atom thick planar sheet of bonded carbon atoms. We have discovered that graphene is a superior hydrophobic support for the generation of artificial lipid monolayers and bilayers because, e.g., graphene can be fabricated into sheets that are atomically thin, strong, relatively chemically inert, and mechanically stable. Although graphene does not conduct ions or electrons from one face to the other, it is electrically conductive in the plane of each face. This in-plane conductivity is sensitive to the environment to which the graphene is exposed.

Graphene can be fashioned to contain small apertures, e.g., having a dimension of millimeter to single nanometer (or less) across, that allow the formation of lipid bilayers. Each face of graphene supports a lipid monolayer, and two monolayers may contact and form lipid bilayers in apertures in the graphene. Because graphene is atomically thin, the dislocation between the graphene supported lipid molecules on each of its faces and the lipid molecules forming a lipid bilayer is minimal. This configuration creates a robust, giga-ohm seal between the bilayer and the graphene.

Molecules (e.g., membrane proteins) can be incorporated into a bilayer in an aperture in graphene. Such structures are useful for investigating and determining the structural and functional properties of, e.g., incorporated membrane proteins. Also, pores can be incorporated into a bilayer aperture in graphene. Such structures are useful for investigating and determining the structure of polymers (e.g., the sequence of a nucleic acid). In order to monitor such structural and functional properties, the invention may include suitably patterned, electrically connected graphene that can transmit electrical currents, including in plane current measurements such as tunneling currents, to traverse the central hydrophobic region of the transmembrane proteins to monitor or alter membrane activity.

Alternatively, a lipid monolayer may be formed on one face of graphene by having oil or another hydrophobic medium on one side of the aperture and water or another hydrophilic medium on the other side. A lipid monolayer within an aperture in graphene would then separate the hydrophobic and hydrophilic media. The interaction of molecules with this interface between media can be measured, e.g., using electrical or optical detection as described herein.

Lipid Bilayers

The invention features lipid bilayers disposed within graphene apertures. In one method of making bilayers, lipid monolayers are disposed on both faces of graphene resulting in a lipid bilayer spontaneously forming within apertures in the graphene. In another method, liposomes disposed on both sides of the graphene are induced to rearrange into lipid bilayers within apertures.

Figure 1:
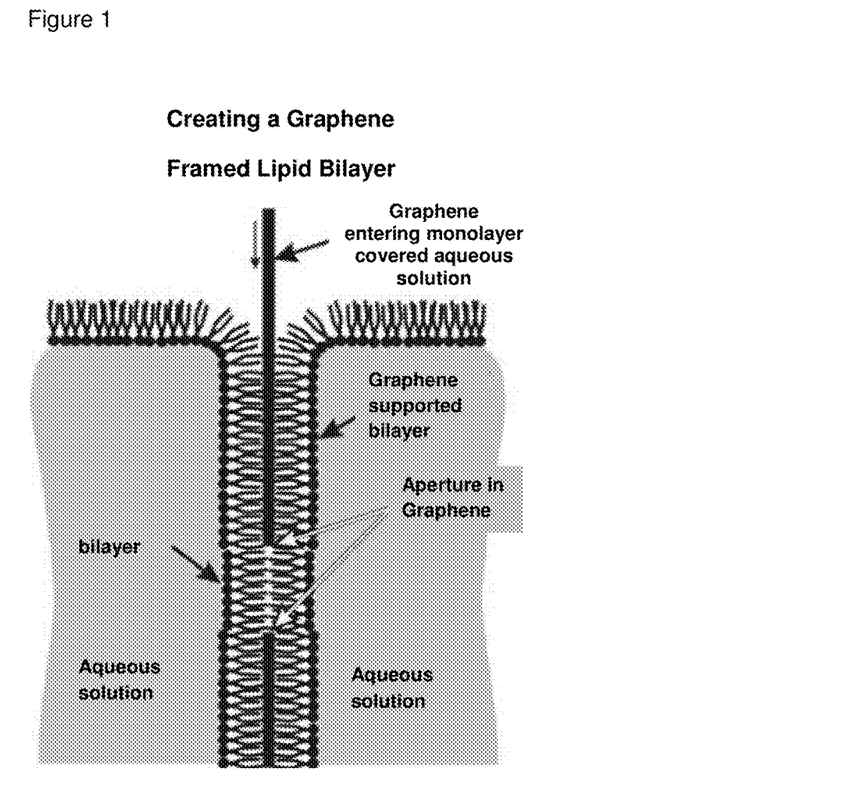
FIG. 1 is a schematic showing the creation of a lipid bilayer by adapting the method of Montal and Muller (Proc Nat Acad Sci 69, 3561-3566 (1972)) for use on graphene.
Figure 2:
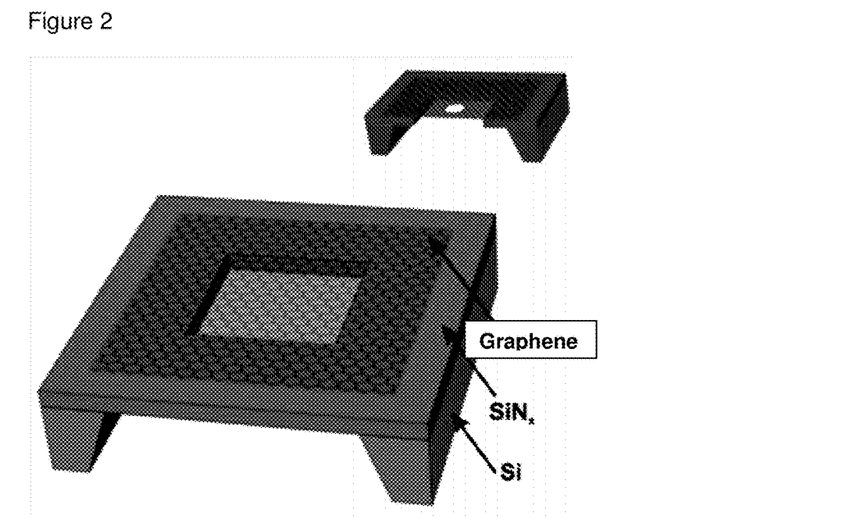
FIG. 2 is a schematic diagram of graphene mounted on a frame such that both faces of the graphene are accessible. Inset: similarly mounted graphene into which a single aperture has been drilled.
Figure 3:
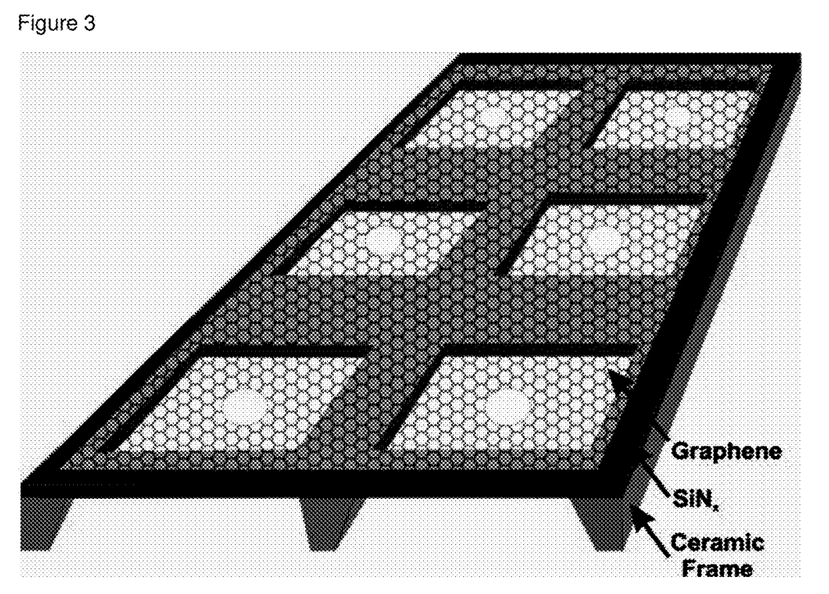
FIG. 3 is a schematic diagram of a structure for forming an array of graphene-supported lipid bilayers (not to scale). A 2×3 array of six nanopores is shown, each of which supports a lipid bilayer. Each compartment in the underlying non-conductive ceramic frame may form a separate solution compartment equipped with an electrode (e.g., Ag—AgCl), with a common ground electrode on the opposite side of the graphene supported bilayers.

In one embodiment, a bilayer can be created using a procedure adapted from Montal and Muller (Proc Nat Acad Sci U.S.A. 69, 3561-3566 (1972)). In the present invention graphene, which can be supported on a rigid frame, is slowly immersed into a solution in a Langmuir-Blodgett trough with a solution-air interface covered with a lipid monolayer maintained at constant pressure (see FIG. 1). FIGS. 2 and 3 show graphene mounted on a suitable frame. As the graphene mounted on its frame penetrates through the lipid-covered solution-air interface, a monolayer of lipid is transferred to each of the two faces of the graphene. Furthermore, a lipid bilayer (whose leaflets are continuous with the two leaflets now covering each side of the graphene) can be induced to self assemble across apertures (nano to micro in size) in the graphene. The graphene can be supported by a frame to form two aqueous compartments. Here, a lipid bilayer in the graphene aperture will represent the thinnest portion separating the two aqueous compartments.

Figure 5:
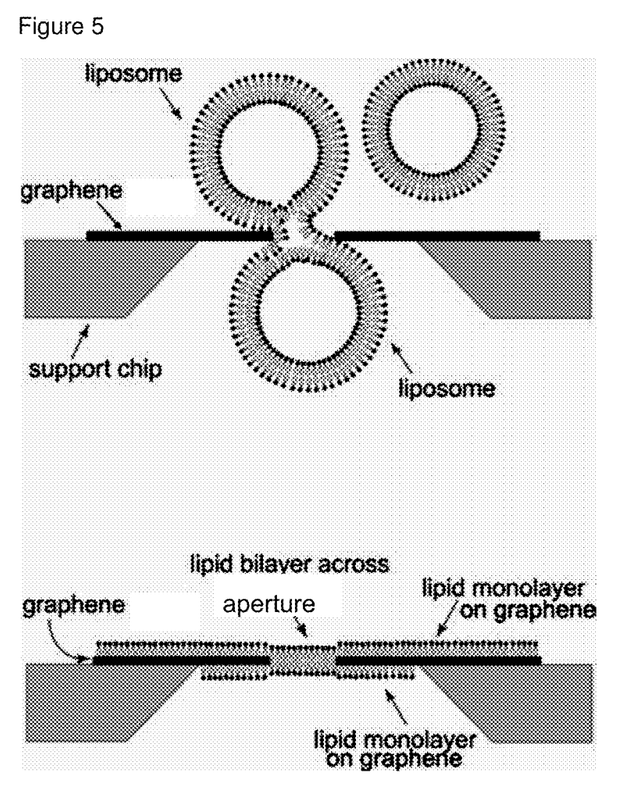
FIG. 5 is a schematic diagram of the use of membrane fusion to form a graphene-supported bilayer.

In another embodiment, a graphene supported bilayer is created by exposing both faces of the graphene to solutions containing unilamellar liposomes whose diameters are greater than the diameter of an aperture in the graphene. Because intact liposomes (whose outer surfaces are hydrophilic) are unlikely to bind to the hydrophobic graphene surface, some liposomes fuse with each other across the apertures in the graphene (FIG. 5, top). This fusion results in molecular rearrangements and structural disruptions creating a monolayer of lipid on each face of the graphene and a bilayer within an aperture (FIG. 5, bottom).

In this embodiment, triggered fusion may be desirable so that the intact pre-fusion liposomes can be introduced on both sides of the graphene membrane in a solution prior to the addition of the triggering agent (e.g., $Ca^{++}$). Millimolar concentrations of $Ca^{++}$ can be added to liposomes composed of 1:1 mole ratios of phosphatidylethanolamine:phosphatidylserine to trigger the fusion of two liposomes. Bilayers and monolayers of lipid could also be formed on only one face of the graphene by standard methods known in the art, e.g., as disclosed in Cooper (J. Mol. Recognit. 17, 286-315 (2004)).

The lipid bilayers can include saturated and unsaturated lipids. Additional examples of lipids are phospholipids (e.g., phosphatidylcholine, phosphatidylserine, phosphatidylethanolamine, and phosphatidylglycerol), glycolipids, and sphingolipids (e.g., sphingomyelin and sterols). Lipids may also be conjugated to other molecules, e.g., at the polar head.

The bilayers are artificial in the sense that they are not attached to a living cell. Membranes or components from an organism, e.g., eukaryotic (e.g., plant, fungal, protist, or animal), prokaryotic, or virus may or may not be employed.

Graphene Apertures

Apertures in graphene are, e.g., nanometer- to micron-sized holes. Apertures useful in the invention typically range in width, i.e., across the aperture, from 1-1000 nm, e.g., at most 750, 500, 400, 300, 250, 200, 150, 100, 90, 80, 70, 60 50, 40, 30, 20, 10, 9, 8, 7, 6, 5, 4, 3, or 2 nm and at least 2, 3, 4, 5, 6, 7, 8, 9, 10, 20, 30, 40, 50, 60, 70, 80, 90, 100, 150, 200, 250, 300, 400, 500, or 750 nm. The through dimension is controlled by the thickness of the graphene. This thickness can be increased by employing a stack of graphene sheets, e.g., 2-5 sheets. The dimensions and shapes of the aperture employed will depend on the intended application.

Figure 4:
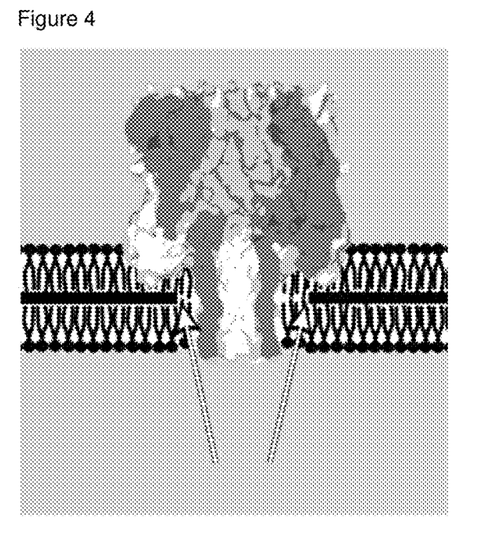
FIG. 4 is a schematic showing α-hemolysin, a transmembrane protein, inserted into a lipid bilayer through an aperture in graphene. If the aperture is drilled to an appropriate dimension (for α-hemolysin ca. 5 nm), its proximity to the stem of the transmembrane protein (arrows) makes it possible for a highly localized field to be applied around the transmembrane portion of the inserted protein and makes it further possible for conformational and other functional protein alterations to be sensed by changes in the graphene's in-plane conductivity and/or other electrical properties.
Figure 7:
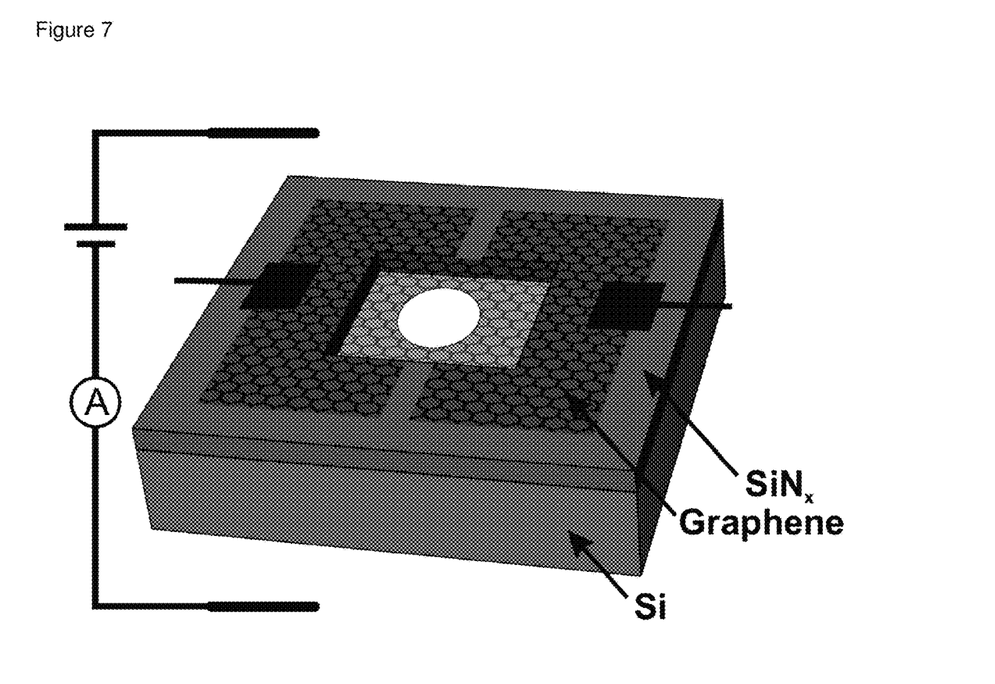
FIG. 7 is a schematic diagram of graphene mounted on a $SiN_x$/Si frame. Portions of the graphene near the aperture have been ablated. The diagram also shows two electrodes mounted on the same face of the graphene.

In certain embodiments, an aperture is sized to maximize the proximity and contacts between a transmembrane protein and the graphene. For example, an aperture between 4.5-5.5 nm across is suitable to accommodate the 4.4 nm diameter transmembrane stem of α-hemolysin (FIG. 4). Thus, an aperture may have a dimension that is no more than 5, 4, 3, 2, 1, 0.5, 0.25, or 0.1 nm wider than the diameter of a transmembrane protein. Excess graphene in the region of the aperture may also be removed with a focused electron beam or ion beam, as shown in FIG. 7. Thus, in certain embodiments, the aperture is disposed in a region of the graphene that is no more than 0.5, 1, 2, 3, 4, 5, 10, 20, 30, 40, or 50 nm wider than the aperture.

Apertures can be sized to accommodate the passage of particular polymers, e.g., polynucleotides, polypeptides, and polysaccharides. For example, an aperture of approximately 0.5-2.0 nm across is suitable for the passage of single stranded DNA; an aperture of 1.0-3.0 nm across is suitable for the passage of double stranded DNA; and an aperture of 1.0-4.0 nm across is suitable for the passage of polypeptides.

Because transmembrane proteins can fully insert or self-assemble only in bilayer regions, an array of apertures in the graphene will create an array of lipid bilayers containing membrane proteins inserted into these bilayers in the same pattern with the same intermolecular spacing as the array of graphene apertures. Furthermore, because graphene can be electrically contacted and is electrically conductive within the plane of each face, the central hydrophobic region of the transmembrane proteins inserted into these unsupported lipid bilayers can be subjected to highly localized electrical fields without disrupting the lipid environment (FIG. 4).

Because of the strength and mechanical stability of graphene, apertures a single nanometer across can be fabricated (using, e.g., electron or ion beams) either singly or in arrays (FIG. 3), with any desired spacing, and are capable of supporting stable lipid bilayers.

Membrane Molecules

Molecules may be disposed within the lipid bilayers formed in apertures in graphene. The molecules can be pore-forming proteins (e.g., ion channels and voltage gated channels) or transmembrane proteins (e.g., transmembrane receptors).

Examples of pore-forming proteins that can be used in the invention include Gramicidin (e.g., Gramicidin A from *Bacillus brevis*; available from Fluka, Ronkonkoma, N.Y.); LamB (maltoporin), OmpF, OmpC, or PhoE from *E. coli, Shigella*, and other Enterobacteriaceae, α-hemolysin (from *S. aureus*), Tsx, the F-pilus, lambda exonuclease, MspA, and mitochondrial porin (VDAC). Homologs and paralogs of these pores may also be employed.

A modified voltage-gated channel can also be used in the invention. Voltage gated channels include voltage-dependent calcium channels, voltage-gated sodium channels, voltage-gated potassium channels, and voltage-gated proton channels. Methods to alter inactivation characteristics of voltage gated channels are well known in the art (see e.g., Patton, et al., Proc. Natl. Acad. Sci. USA, 89:10905-09 (1992); West, et al., Proc. Natl. Acad. Sci. USA, 89:10910-14 (1992); Auld, et al., Proc. Natl. Acad. Sci. USA, 87:323-27 (1990); Lopez, et al., Neuron, 7:327-36 (1991); Hoshi, et al., Neuron, 7:547-56 (1991); Hoshi, et al., Science, 250: 533-38 (1990), all hereby incorporated by reference).

Pores can be formed in a lipid bilayer using chemicals (or peptides) such as Nystatin, as is well known in the art of whole-cell patch clamping ("perforated patch" technique), and peptide channels such as Alamethicin.

Pore-forming proteins can also be linked to molecular motors (e.g., a polymerase or exonuclease). Here, synthetic/recombinant DNA coding for a fusion protein can be transcribed and translated, then inserted into the lipid bilayer region of the artificial membranes of the invention. For example, the C-terminus of *E. coli* DNA polymerase I (and by homology, T7 DNA polymerase) is very close to the surface of the major groove of the newly synthesized DNA. If the C-terminus of a polymerase is fused to the N-terminus of a pore forming protein such as colicin E1 and the colicin is inserted into an artificial membrane, one opening of the colicin pore should face the DNA's major groove and one should face the opposite side of the lipid bilayer. The colicin molecule can be modified to achieve a pH optimum compatible with the polymerase as in Shiver et al. (J. Biol. Chem., 262:14273-14281 1987, hereby incorporated by reference). Both pore and polymerase domains can be modified to contain cysteine replacements at points such that disulfide bridges form to stabilize a geometry that forces the pore opening closer to the major groove surface and steadies the polymer as it passes the pore opening. The loops of the pore domain at this surface can be systematically modified to maximize sensitivity to changes in the DNA sequence.

Transmembrane receptors include cytokine receptors (e.g., IL-2 receptor, interferon alpha/beta receptor, interferon gamma receptor, erythropoietin receptor, GM-CSF receptor, G-CSF receptor, growth hormone receptor, prolactin receptor, oncostatin M receptor, and leukemia inhibitory factor receptor), members of the immunoglobin superfamily (e.g., interleukin-1 receptor, CSF1, C-kit receptor, and interleukin 18 receptor), members of the tumor necrosis factor receptor family (e.g., CD27, CD30, CD40, CD120, and lymphotoxin beta receptor), chemokine receptors (interleukin-8 receptor, CCR1, CXR4, MCAF receptor, and NAP-2 receptor), receptor tyrosine kinases (e.g., erythropoietin receptor, insulin receptor, Eph receptors, and insulin-like growth factor 1 receptor), TGF beta receptors (e.g., TGF beta receptors 1 and 2), and other G-protein coupled receptors.

Additional molecules include ion channels and pumps, e.g., multidrug resistance pumps.

Molecular Motors

Any molecular motor that is capable of moving a polymer (e.g., a polynucleotide) of interest may be employed in the invention. Desirable properties of a molecular motor include: sequential action, e.g., addition or removal of one nucleotide per turnover; no backtracking along the target polymer; no slippage of the motor on the target polymer due to forces, e.g., from an electric field, employed to drive a polymer to the motor; retention of catalytic function when disposed adjacent an aperture; high processivity, e.g., the ability to remain bound to a target polymer and perform at least 1,000 rounds of catalysis before dissociating.

Molecular motors include, e.g., polymerases (i.e., DNA and RNA), helicases, ribosomes, and exonucleases. The molecular motor that is used according to the methods described herein will depend, in part, on the type of target polymer being analyzed. For example, a molecular motor such as a DNA polymerase or a helicase is useful when the target polynucleotide is DNA, and a molecular motor such as RNA polymerase is useful when the target polynucleotide is RNA. In addition, the molecular motor used will depend, in part, on whether the target polynucleotide is single-stranded or double-stranded. Those of ordinary skill in the art would be able to identify the appropriate molecular motors useful according to the particular application.

DNA polymerases have been demonstrated to function as efficient molecular motors. Exemplary DNA polymerases include E. coli DNA polymerase I, E. coli DNA polymerase I Large Fragment (Klenow fragment), phage T7 DNA polymerase, Phi-29 DNA polymerase, thermophilic polymerases (e.g., Thermus aquaticus (Taq) DNA polymerase, Thermus flavus (Tfl) DNA polymerase, Thermus Thermophilus (Tth) DNA polymerase, Thermococcus litoralis (Tli) DNA polymerase, Pyrococcus furiosus (Pfu) DNA polymerase, Vent DNA polymerase, or Bacillus stearothermophilus (Bst) DNA polymerase), and a reverse transcriptase (e.g., AMV reverse transcriptase, MMLV reverse transcriptase, or HIV-1 reverse transcriptase). Other suitable DNA polymerases are known in the art. In one embodiment, approximately 300 nucleotides per second are threaded through the clamp of a DNA polymerase in a ratchet-like linear fashion, which decreases the probability of backward movement of the polynucleotide. In certain embodiments, E. coli DNA polymerase I, the Klenow fragment, phage T7 DNA polymerase, Taq polymerase, and the Stoffel fragment are excluded from the molecular motors employed in the invention.

RNA polymerases, like DNA polymerases, can also function as efficient molecular motors. Exemplary RNA polymerases include T7 RNA polymerase, T3 RNA polymerase, SP6 RNA polymerase, and E. coli RNA polymerases. In certain embodiments, T7 RNA polymerase is excluded from the molecular motors employed in the invention.

The molecular motor may also include a single-strand specific or double-strand specific exonuclease. Lambda exonuclease, which is itself shaped as a pore with a dimension similar to α-hemolysin, can operate as a motor, controlling the movement of the nucleic acid polymer through the channel. Exonuclease Lambda is a trimeric enzyme isolated from the E. coli bacteriophage Lambda, and is particularly well suited for use in the methods and devices of the invention for a number of reasons. It acts upon double-stranded DNA, which is a preferred substrate for genetic analysis. Also, it is a highly processive enzyme and acts upon only one strand of the double-stranded DNA, which facilitates the movement of a given DNA molecule with respect to an aperture. Further, the digestion rate is about 10-50 nucleotides per second (van Oijen et al. Science 301:1235 (2003); Perkins et al. Science 301:1914 (2003)). As the double stranded polymer passes through the pore, the exonuclease grabs onto the 5' single-stranded overhang of a first strand (via endonuclease digestion or breathing of the double stranded DNA ends) and sequentially cleaves the complementary second strand at its 3' end. During the sequential cleavage, the exonuclease progresses 5' to 3' down the first strand, pulling the double stranded DNA through the channel at a controlled rate. Thus, the exonuclease can operate as a pore as well as a motor for drawing the nucleic acid polymer through the channel. Exonuclease Lambda may also be excluded from the molecular motors employed in the invention. Additional exonucleases include, for example, T7 Exonuclease, Exo III, RecJ$_1$ Exonuclease, Exo I, and Exo T.

Another type of molecular motor is a helicase. Helicases are proteins, which move along polynucleotide backbones and unwind the polynucleotide so that the processes of DNA replication, repair, recombination, transcription, mRNA splicing, translation, and ribosomal assembly, can take place. Helicases include both RNA and DNA helicases. Helicases have previously been described in U.S. Pat. No. 5,888,792. Exemplary helicases include hexameric helicases such as the E-coli bacteriophage T7 gp4 and T4 gp41 gene proteins, and the E. coli proteins DnaB, RuvB, and rho (for review see: West S C, Cell, 86, 177-180 (1996)). Hexameric helicases unwind double stranded DNA in a 5'-3' direction, which ensures a directional analysis of the DNA target molecules. In addition, some of the helicases have processive translocation rates in excess of 1000 nucleotides per second (Roman et al. J. Biol. Chem. 267:4207 (1992). In addition, these hexameric helicases form a ring structure having an inside hole dimension ranging in size from 2-4 nanometers and an outside ring dimension of about 14 nanometers, which is within the dimension limits of a useful molecular motor. The hexameric ring structure is formed and stabilized in the presence of $Mg^{+2}$ and some type of nucleotide (NMP, NDP or NTP).

The intrinsic rate of movement of a particular molecular motor may be modified, e.g., by chemical modification of the motor, by changes in temperature, pH, ionic strength, the presence of necessary cofactors, substrates, inhibitors, agonists, or antagonists, by the nature of the medium (e.g., the presence of nonaqueous solvents or the viscosity), by external fields (e.g., electric or magnetic fields), and hydrodynamic pressure. Such modifications may be used to start, stop, increase, decrease, or stabilize the rate of movement, which may occur during a particular characterization. In addition, such modifications may be used as switches, brakes, or accelerators, e.g., to start, stop, increase, or decrease movement of a polynucleotide. In alternative embodiments, external forces (e.g., electric or magnetic fields or hydrodynamic pressure) generated other than by molecular motors may be used to control the rate of movement. The rate of movement may be substantially slowed or even stopped (e.g., paused) before, during, or after analysis of a particular polynucleotide.

A molecular motor may be disposed on the cis or trans side of a graphene supported lipid bilayer. In either case, the molecular motor can be adjacent the pore or inline with the pore. A molecular motor may also be wholly or partially disposed within a graphene aperture. A molecule motor may be conjugated to a lipid in the bilayer or to another molecule disposed in the bilayer, e.g., a non-pore forming protein or sterol.

Detection System

The invention features assays and devices for detecting properties of compounds using lipid bilayers. In one series of embodiments, the bilayers of the invention contain membrane molecules (e.g., transmembrane proteins and pores). Compounds are then administered to the bilayers and at least one property of the molecule is measured (directly or indirectly by the effect on the compound). Such properties can include electrical properties, e.g., effect on conductance. In another series of embodiments, the bilayers of the invention are used to identify the properties of a polymer (e.g., the sequence or length of a polynucleotide). In this series of embodiments, a pore-forming molecule is disposed in the lipid bilayer, and a property, e.g., electrical conductance across or through the pore, is measured as a polymer moves with respect to the pore (e.g., by passing across or through the pore). The invention may also be employed in the study of organisms (e.g., cells or viruses) with the bilayer or components thereof.

A typical detection system includes electronic equipment capable of measuring characteristics of the compound, e.g., a polynucleotide, as it interacts with the pore or other membrane molecules, a computer system capable of controlling the measurement of the characteristics and storing or displaying the corresponding data, and one or more detectors capable of measuring at least one property of compounds, pores, other membrane molecules, or graphene in the device.

The detection system can measure transport properties, such as, but not limited to, the amplitude or duration of individual conductance or electron in plane current, such as tunneling current, changes across or through an aperture or pore.

In one embodiment, the detection system can be used to determine the nature or length of a polymer (e.g., a polynucleotide). Changes in the electrical properties of a pore can identify the monomers in sequence, as each monomer has a characteristic conductance change signature, or a change in the conformation of a transmembrane protein. For instance, the volume, shape, or charges on each monomer can affect conductance in a characteristic way. Likewise, the size of the entire polymer can be determined by observing the length of time (duration) that monomer-dependent conductance changes occur. Alternatively, the number of monomers in a polymer (also a measure of size) can be determined as a function of the number of monomer-dependent conductance changes for a given polymer traversing the aperture. The number of monomers may not correspond exactly to the number of conductance changes, because there may be more than one conductance level change as each monomer of polymer passes sequentially through or across the aperture. However, there is a proportional relationship between the two values that can be determined by preparing a standard with a polymer having a known sequence. Other detection schemes are described herein.

Exemplary detection components have been described in WO 2009/045473, WO 2009/045472, WO 2008/124107, WO 2007/084163, WO 06/052882, WO 06/028508, WO 05/061373, WO 04/077503, WO 03/003446, WO 03/000920, WO 01/42782, WO 00/28312, and WO 00/79257, each of which is incorporated by reference in its entirety, and can include, but are not limited to, electrodes directly associated with the structure at or near the aperture, and electrodes placed within the cis and trans pools. The electrodes can be capable of, e.g., detecting ionic current differences between the two pools or in plane currents, such as electron tunneling currents, across or through the pore or aperture. As described above, a frame can be disposed to create discrete chambers on one or both faces of the graphene, and each chamber may include an electrode. In this embodiment, the electrical property, e.g., conductance, of individual apertures disposed in an array can be separately measured allowing the simultaneous detection of the activities associated with numerous polymers or transmembrane proteins.

Time-dependent properties of the aperture may be measured by any suitable technique. The properties may be a function of the medium used in the assay, solutes (e.g., ions) in the liquid, the polymer (e.g., chemical structure of the monomers), or labels on the polymer. Exemplary transport properties include current, conductance, resistance, capacitance, charge, concentration, optical properties (e.g., fluorescence and Raman scattering), and chemical structure.

Desirably, the transport property is current. Suitable methods for detecting current in aperture containing systems are known in the art, for example, as described in U.S. Pat. Nos. 6,746,594, 6,673,615, 6,627,067, 6,464,842, 6,362,002, 6,267,872, 6,015,714, and 5,795,782 and U.S. Publication Nos. 2004/0121525, 2003/0104428, and 2003/0104428, each of which is incorporated by reference in its entirety. In another embodiment, the transport property is electron flow across the aperture, which may be monitored by electrodes disposed adjacent to or abutting the aperture boundary.

Additional methods of detecting the interaction of compounds with pore proteins suitable for use in the devices and methods of the invention are outlined in Bayley and Cremer, Nature 413:226-229 (2001) which is hereby incorporated by reference in its entirety.

Media

The medium disposed in the compartments on either side of the graphene may be any fluid that permits adequate substrate interaction (e.g., polynucleotide mobility). Typically, the medium is a liquid, usually aqueous solutions or other liquids or solutions in which the polymers or compounds can be distributed. When an electrically conductive medium is used, it can be any medium that is able to carry electrical current. Such solutions generally contain ions as the current-conducting agents (e.g., sodium, potassium, chloride, calcium, magnesium, cesium, barium, sulfate, or phosphate). Conductance across or through the aperture can be determined by measuring the flow of current across or through the aperture via the conducting medium. Alternatively, an electrochemical gradient may be established by a difference in the ionic composition of the two pools of medium, either with different ions in each pool, or different concentrations of at least one of the ions in the solutions or media of the pools. Conductance changes are measured by the detection system.

Methods of Characterizing Polymers

In general, the invention features characterization of polymers involving the use of two separate pools of a medium and an interface between the pools. The aperture between the pools is typically capable of interacting sequentially with the individual monomer residues of a polymer present in one of the pools. Measurements of transport properties are continued over time, as individual monomer residues of the polymer interact sequentially with the aperture, yielding data suitable to determine a monomer-dependent characteristic of the polymer. The monomer-dependent characterization achieved by sequencing may include identifying characteristics such as, but not limited to, the number and composition of monomers that make up each individual polymer, in sequential order.

The polymer being characterized may remain in its original pool or it, or a reaction product including it or fragments thereof, may cross the pore into the other pool. In either situation, the polymer moves in relation to the pore, and individual monomers interact sequentially with the pore, giving rise to a change in the measured transport properties, e.g., conductance, of the pore. When the polymer does not cross into the trans side of the device, it is held adjacent the pore such that its monomers interact with the pore passage and bring about the changes in transport properties, which are indicative of polymer characteristics.

Polymers can be driven through the pore with or without the assistance of a molecular motor. The rate is controlled by the use of a molecular motor that moves a polymer at a substantially constant rate, at least for a portion of time during a characterization. In the absence of a molecule motor, the polymer can be driven through the pore using, e.g., an electric current or pressure.

Methods of Identifying Transmembrane Protein-Interacting Compounds

The bilayers of the invention can also be used to identify compounds that interact with membrane molecules (e.g., pore-forming proteins or transmembrane receptors). Here, a property (e.g., electrical conductance) of a transmembrane protein disposed inside a graphene aperture can be measured in the presence and absence of a candidate compound. If the addition of a compound changes a property of the transmembrane protein, the compound is identified as a transmembrane protein-interacting compound. This method can include contacting the transmembrane protein with a positive or negative control compound (e.g., a known ligand for a transmembrane receptor). In these embodiments, a property of the transmembrane protein in the presence of the control compound can be measured, and a candidate compound that enhances or disrupts such a property can be identified as being a transmembrane protein-interacting compound.

In another embodiment, the transmembrane protein can be a pore-forming protein and candidate compounds can be tested to disrupt the flow of molecules through the pore. The flow of molecules through the pore can be measured using, e.g., a measurement of electric current through or across the aperture.

Known interacting compounds may also be employed to measure the property of transmembrane proteins.

In addition, the methods of the invention may be employed to study the interaction of compounds with lipids, e.g., glycolipids, lipids conjugated to other compounds, or other non-protein compounds in the bilayer. The methods of the invention may also be employed to study the ability of compounds to pass through a lipid bilayer or monolayer, e.g., in transfection or drug delivery, either directly through the lipid layer or through a pore in the layer. Such compounds could be free in solution or part of a complex, e.g., encapsulated in a micelle, vesicle, or liposome.

Example

Liposomes can be triggered to form a lipid bilayer membrane that forms a high resistance giga-ohm seal across an aperture in a graphene membrane that separates two solution filled chambers (FIG. 5).

Figure 6:
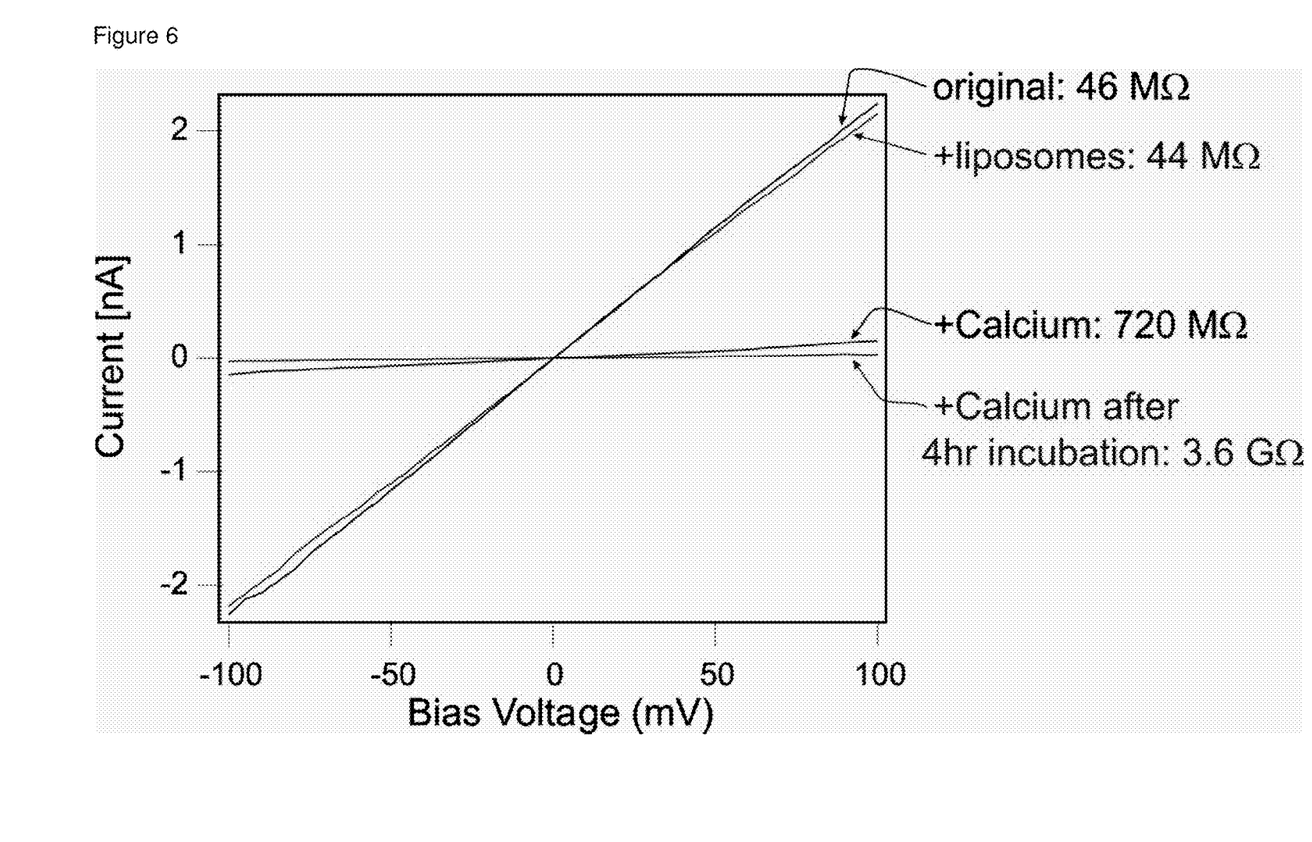
FIG. 6 is a graph showing current as a function of voltage across an 8 nm aperture in graphene under the indicated conditions.

A 0.5×0.5 mm CVD grown sheet of graphene was mounted over a 200×200 nm aperture in a 250 nm thick, free-standing, insulating $SiN_x$ layer on a silicon substrate frame as shown in FIG. 2. The chip-mounted membrane was inserted in a fluidic cell such that it separated two compartments, each subsequently filled with ionic solutions (250 mM KCl, 2.5 mM TRIS, pH 7.8) in electrical contact with Ag/AgCl electrodes. The resistance of the aperture to ionic current flow was then measured by sweeping the voltage bias between the two chambers separated by the chip-mounted graphene from −100 mV to +100 mV. Before adding liposomes, the aperture resistance was 46 MO, which is the expected access resistance of an 8 nm aperture in graphene. Adding liposomes to the chamber on one side of the graphene (not shown) or to the chambers on both sides of the graphene had little effect until lipid fusion was triggered by addition of 2 mM $Ca^{++}$. An increased resistance to 720 MO was observed within seconds after addition of $Ca^{++}$, although incubation for four hours at room temperature further increased the resistance to over 3.6 GΩ (FIG. 6).

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are in the claims.

What is claimed is:

1. A device comprising an artificial membrane spanning one or more apertures on graphene and at least one transmembrane pore disposed in the artificial membrane in one of said one or more apertures, wherein the membrane is a bilayer within the one or more apertures and two monolayers interleaved by the graphene at the peripheral edges of the one or more apertures.

2. The device of claim 1, wherein said transmembrane pore comprises a transmembrane protein.

3. The device of claim 2, wherein said transmembrane protein is selected from the group consisting of ion channels, multidrug resistance pumps, cytokine receptors, receptors from the immunoglobin superfamily, receptors from the tumor necrosis factor receptor family, chemokine receptors, receptor tyrosine kinases, and TGF beta receptors.

4. The device of claim 1, wherein at least one of said pores is α-haemolysin.

5. The device of claim 1, further comprising a frame supporting said graphene.

6. The device of claim 5, further comprising first and second electrodes disposed on opposite sides of said graphene.

7. The device of claim 5, wherein said frame comprises a ceramic or silicon nitride.

8. The device of claim 1, wherein said device comprises a plurality of apertures arranged in an array.

9. The device of claim 8, further comprising a frame positioned on one face of the graphene, wherein said frame forms separate compartments for housing liquid for each of said apertures.

10. The device of claim 9, wherein said frame is non-conductive.

11. The device of claim 9, wherein said frame comprises a ceramic or silicon nitride.

12. The device of claim 9, wherein each of said compartments further comprises an electrode, and wherein said device further comprises at least one electrode on the side of said graphene opposite said compartment.

13. The device of claim 1 wherein the at least one of said pores is OmpF, OmpC or MspA.

14. The device of claim 13 wherein the artificial membrane is a lipid bilayer.

15. The device of claim 1, wherein at most one pore is disposed in each of said one or more apertures.

16. The device of claim 1, further comprising a molecular motor, wherein said motor is adjacent to the transmembrane pore and is capable of moving a polymer with respect to the transmembrane pore.

17. The device of claim 16, wherein the molecular motor comprises a DNA polymerase, a RNA polymerase, a ribosome, an exonuclease, or a helicase and said polymer is a polynucleotide.

18. The device of claim 17, wherein the DNA polymerase is selected from *E. coli* DNA polymerase I, *E. coli* DNA polymerase I Large Fragment (Klenow fragment), phage T7 DNA polymerase, Phi-29 DNA polymerase, *Thermus aquaticus* (Taq) DNA polymerase, *Thermus flavus* (Tfl) DNA polymerase, *Thermus Thermophilus* (Tth) DNA polymerase, *Thermococcus litoralis* (Tli) DNA polymerase, *Pyrococcus furiosus* (Pfu) DNA polymerase, *Bacillus stearothermophilus* (Bst) DNA polymerase, AMV reverse transcriptase, MMLV reverse transcriptase, and HIV-1 reverse transcriptase.

19. The device of claim 17, wherein the RNA polymerase is selected from T7 RNA polymerase, T3 RNA polymerase, SP6 RNA polymerase, and *E. coli* RNA polymerase.

20. The device of claim 17, wherein the exonuclease is selected from exonuclease Lambda, T7 Exonuclease, Exo III, $RecJ_1$ Exonuclease, Exo I, and Exo T.

21. The device of claim 17, wherein the helicase is selected from *E-coli* bacteriophage T7 gp4 and T4 gp41 gene proteins, *E. coli* protein DnaB, *E. coli* protein RuvB, and *E. coli* protein rho.

22. A method of identifying a membrane molecule-interacting compound comprising providing a device comprising an artificial membrane spanning one or more apertures on graphene and said membrane molecule, contacting the membrane molecule with a compound, and measuring at least one activity of said membrane molecule in the presence of said compound, whereby a change in activity in the presence of said compound indicates that said compound interacts with said membrane molecule, wherein said membrane molecule is a transmembrane pore disposed in the artificial membrane in one of said one or more apertures, wherein measuring at least one activity of said membrane molecule in the presence of said compound comprises measuring electric current through or across the one or more apertures, and wherein the membrane is a bilayer within the one or more apertures and two monolayers interleaved by the graphene at the peripheral edges of the one or more apertures.

23. The method of claim 22, wherein membrane molecule-interacting compound is a polymer, and the device further comprises a molecular motor, wherein said motor is adjacent to the transmembrane pore and is capable of moving the polymer with respect to the transmembrane pore.

24. The method of claim 22, wherein the transmembrane pore comprises a transmembrane protein.

* * * * *